(12) United States Patent
Hirabayashi et al.

(10) Patent No.: US 6,774,359 B1
(45) Date of Patent: Aug. 10, 2004

(54) SAMPLE-INTRODUCTION TOOL, AND AN ION SOURCE AND A MASS SPECTROMETER USING THE SAMPLE-INTRODUCTION TOOL

(75) Inventors: Yukiko Hirabayashi, Kokubunji (JP); Atsumu Hirabayashi, Kodaira (JP); Akihiko Okumura, Hachioji (JP); Hideaki Koizumi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/762,276
(22) PCT Filed: Aug. 6, 1998
(86) PCT No.: PCT/JP98/03502
§ 371 (c)(1), (2), (4) Date: Feb. 6, 2001
(87) PCT Pub. No.: WO00/08453
PCT Pub. Date: Feb. 17, 2000

(51) Int. Cl.⁷ .......................... G01N 23/06; H01J 49/00
(52) U.S. Cl. ...................................... 250/287; 250/288
(58) Field of Search ............................... 250/287, 288; 422/99; 356/246

(56) References Cited

U.S. PATENT DOCUMENTS

| | | | | |
|---|---|---|---|---|
| 5,433,344 A | * | 7/1995 | Fulton et al. | 222/65 |
| 5,876,675 A | * | 3/1999 | Kennedy | 422/99 |
| 6,110,343 A | * | 8/2000 | Ramsey et al. | 204/601 |
| 6,396,057 B1 | * | 5/2002 | Jarrell et al. | 250/288 |
| 6,459,080 B1 | * | 10/2002 | Yin et al. | 250/288 |
| 2003/0111599 A1 | * | 6/2003 | Staats | 250/288 |

FOREIGN PATENT DOCUMENTS

JP 08-62200 * 3/1996

OTHER PUBLICATIONS

Analytical Chemistry, 60, pp. 436–441(1988).
Analytical Chemistry, 65, pp. 2637–2642(1993).
Analytical Chemistry, 59, pp. 2642–2646(1987).
Journal of Physical Chemistry, 88, pp. 4451–4459(1984).
Analytical Chemistry, 54, pp. 143–146(1982).
Analytical Chemistry, 66, pp. 4557–4559(1994).
Analytical Chemistry, 67, pp. 2878–2882(1995).
Japanese Patent Laid–Open No. 07–306193(1995).
Japanese Patent Laid–Open No. 08–062200(1996).
Japanese Patent Laid–Oopen No. 08–005624(1996).
Japanese Patent Laid–Open No. 09–243600(1997).

* cited by examiner

Primary Examiner—John R. Lee
Assistant Examiner—James J Leybourne
(74) Attorney, Agent, or Firm—Antonelli, Terry, Stout & Kraus, LLP

(57) ABSTRACT

In a sample-introduction tool in which an end of a passage is connected to a reservoir for storing a mobile phase solution, a sample-dropping orifice is provided at the passage and the mobile phase solution and a sample running off from the other end of the passage are introduced into a mass spectrometer by generating a high-speed gas stream around the other end of the passage. The mobile phase solution and the sample are nebulized by the high-speed gas stream, and the injected sample is ionized.

60 Claims, 12 Drawing Sheets

SAMPLE-INTRODUCTION TOOL, AND AN ION SOURCE AND A MASS SPECTROMETER USING THE SAMPLE-INTRODUCTION TOOL

BACKGROUND OF THE INVENTION

1. Field of the Invention

The present invention relates to a sample-introduction tool for introducing a sample solution into an analyzer or for melting a frozen sample with a solvent and introducing the melted sample into an analyzer. More particularly, the invention relates to a small sample-introduction tool which is formed on a substrate made of silicon or quartz and can continuously introduce a small amount of samples at high speed. The invention also relates to a mass spectrometer which can be connected to the sample-introduction tool.

2. Description of the Related Arts

A capillary electrophoresis apparatus (CE) and a liquid chromatograph (LC) can separate a sample substance dissolved in a solution but it is hard for them to identify the kind of a separated sample substance. On the other hand, a mass spectrometer (MS) can identify a sample substance with high sensitivity, but cannot separate a sample substance dissolved in a solution. In the case of separating and analyzing a plurality of sample substances dissolved in a solvent such as water, capillary electrophoresis/mass spectrometer (CE/MS) in which a capillary electrophoresis apparatus is coupled to a mass spectrometer or liquid chromatograph/mass spectrometer (LC/MS) in which a liquid chromatograph is coupled to a mass spectrometer is generally used.

The CE/MS is described in "Analytical Chemistry", 60, pp. 436–441 (1988).

A technique of forming a narrow groove on a glass substrate and performing electrophoresis via the groove to thereby separate mixed samples from each other is described in "Analytical Chemistry", 65, pp. 2637–2642 (1993).

In order to analyze a sample substance separated by the capillary electrophoresis apparatus or liquid chromatograph by a mass spectrometer, it is necessary to transform the sample molecules in the solution to gaseous ions. Known conventional techniques for obtaining such gaseous ions are ion spray ionization (Analytical Chemistry, 59, pp. 2642–2646 (1987)), the electro spray ionization (Journal of Physical Chemistry, 88, pp. 4451–4459 (1984)), atmospheric pressure ionization (Analytical Chemistry, 54, pp. 143–146 (1982)), and the like.

As ionization different from the above conventional techniques, sonic spray ionization capable of efficiently generating gaseous ions only by spraying a sample solution by a sonic gas stream has been recently reported (Analytical Chemistry, 66, pp. 4557–4559 (1994), Analytical Chemistry, 67, pp. 2878–2882 (1995), and Japanese Unexamined-Patent Application Nos. 07-306193 and 08-062200). In the ionization, it is considered that small charged droplets are generated by a sonic gas stream and solvent molecule are peeled off from the charged droplets, thereby generating gaseous ions of the sample molecules.

A method of continuously introducing a small amount of samples by gravity without using a liquid chromatography or a solution sending pump at the time of introducing a sample into the mass spectrometer is disclosed in Japanese Unexamined Patent Application No. 08-005624. Further, a capillary electrophoresis/mass spectrometer which eliminates the need for providing a solution sending pump of a nebulization auxiliary solution by applying the sonic spray ionization to an ion source is disclosed in Japanese Unexamined Patent Application No. 09-243600.

In the case of introducing a sample solution to an analyzer such as a liquid chromatograph/mass spectrometer (LC/MS), a method of injecting a sample to a passage through which a mobile phase solution is flowing by a pump or the like connected to a syringe or autosampler is conventionally used. A sample-introduction passage to which a syringe is fit or a sample-introduction passage of the autosampler is branched from a mobile phase passage, and the flow of a solution is switched by a valve or the like. Since the valve is in contact with the sample solution, it is apt to be unclean and it often causes what is called contamination in which a sample component introduced last time is mixed with a sample of this time. Since it is necessary to switch the valve, inject samples, and again switch the valve for each sample introduction, in the case of analyzing a number of kinds of samples, it takes very long time.

In the case of using a mass spectrometer as an analyzer of an introduced sample, the inside of the mass spectrometer is not resistive to contamination and the sensitivity deteriorates when it becomes contaminated, so that the inside of the mass spectrometer has to be periodically cleaned. Consequently, in the conventional sample introducing method, it is difficult to perform analysis continuously for long time. In order to clean the inside of the mass spectrometer, the inside of the mass spectrometer which is kept in vacuum during analysis has to be exposed to atmosphere, so that it takes long time to re-obtain a degree of vacuum at which analysis can be performed. When the interval of cleaning is short, a problem such that analysis throughput considerably deteriorates arises.

SUMMARY OF THE INVENTION

It is, therefore, an object of the invention to provide a sample-introduction tool capable of continuously or intermittently introducing samples into a solution of constant flow velocity without requiring a valve for switching a passage to prevent contamination as described above and capable of improving analysis throughput by shortening time required to introduce samples.

Another object of the invention is to provide a mass spectrometer which can be connected to the sample-introduction tool according to the invention and can conduct high-speed analysis on a sample introduced at high speed.

When a mobile phase solution is sent by applying pressure to the passage inlet by a pump or the like and a sample is also introduced by applying pressure as in a conventional manner, if the passage is not switched to pass the solution only to one of the passages, the solution flows backward to the other passage. Consequently, a passage switching valve is necessary. In the present invention, the pressure on the outlet side of the passage is reduced and the solution is pumped by the pressure difference between the reduced pressure and the pressure on the passage inlet side. With such a construction, even when a sample-introduction passage is branched from a passage and a valve is not provided at the branch, the solution does not flow backward. Further, even when an end portion of the sample-introduction passage is opened, the mobile phase solution does not flow backward, so that samples can be sequentially charged while the end portion of the sample-introduction passage remains open. Thus, analysis throughput can be improved.

In order to minimize contamination in the mass spectrometer and reduce the number of cleaning times so that analysis

DESCRIPTION OF THE PREFERRED EMBODIMENTS

Embodiments of the invention will be described in detail hereinbelow with reference to the drawings.

<First Embodiment>

Figure 1:
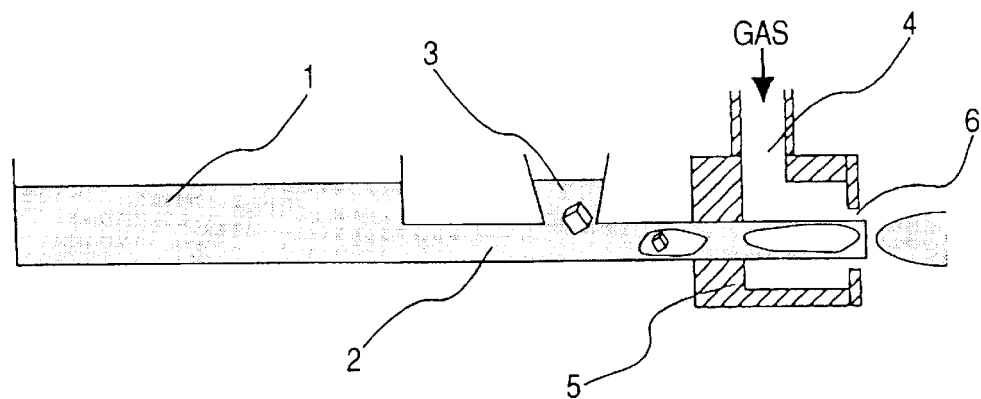
FIG. 1 is a cross section showing the basic construction of a sample-introduction tool as a first embodiment of the invention.

FIG. 1 shows the construction of a tool as an embodiment of the invention. In the drawing, the bottom portion of a reservoir 1 is connected to one end (inflow end) of a tubular passage 2. At the passage 2, a sample-dropping orifice 3 is provided. At the other end (outflow end) of the passage 2, an ion source or nebulizer 5 is disposed. The tip of the passage 2 is inserted to an orifice 6 of the ion source or nebulizer 5. In this case, the ion source 5 plays the role of a nebulizer according to the purpose. The ion source 5 plays both roles of the ion source and the nebulizer according to the purpose. A solution spraying gas flows from a gas supply source (not shown) on the outside through a gas passage 4 into the ion source 5, flows around the passage 2, and runs off from the orifice 6 to the outside atmosphere (normal atmosphere). When the speed of the outflow gas is high, the pressure around the tip of the passage 2 is reduced, and a pressure difference occurs between the reduced pressure and the outside atmospheric pressure (normal atmosphere) near the reservoir 1. By the pressure difference, a mobile phase solution in the reservoir 1 is pumped into the passage 2 and sent through the passage 2 to the tip of the passage 2, and the solution running off from the passage 2 is sprayed (atomized) by a high-speed gas stream from the orifice 6. The sample dropped from the sample-dropping orifice 3 is also pumped into the passage 2 by the pressure difference between the pressure around the orifice 3 and the pressure around the tip of the passage 2, sent together with the mobile phase solution to the tip of the passage 2, and is nebulized. When the speed of the stream of the spray gas is high, the injected sample is ionized, and the function as the ion source is performed.

A sample may be a liquid sample or a solid state sample obtained by freezing a liquid sample. In the case of the liquid sample, the liquid has surface tension, so that it is difficult to reduce the amount of a droplet injected per time to be smaller than the order of a microliter. However, in the case of the solid state sample obtained by freezing a liquid sample, there is no influence of the surface tension. The injection amount per time can be therefore reduced to the order of a nanoliter. In the case of such a small frozen sample, it is immediately melted after it is dropped into a mobile phase solution, so that there is no interfere with ionization.

Figure 2:
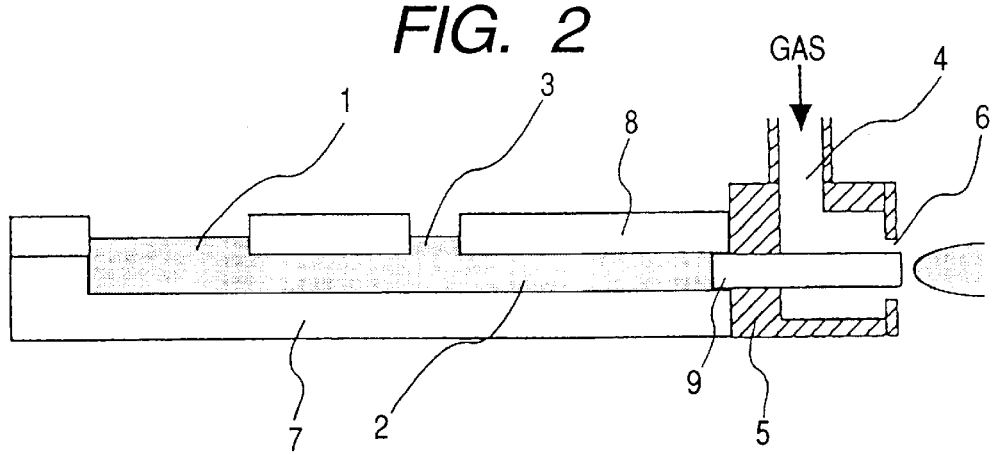
FIG. 2 is a cross section showing the construction of a modification of the sample-introduction tool as the first embodiment of the invention.

FIG. 2 shows the construction of a modification, of the embodiment of FIG. 1, in which the reservoir 1, passage 2 and the like are formed by grooving a substrate 7 and, by adhering the substrate 7 and an operculiform part 8 for sealing to each other, the passage 2 is allowed to have a sealed structure. In the substrate 7, a recess serving as the reservoir 1 and a groove serving as the passage 2 are etched. On the substrate 7, the operculiform part 8 for sealing having openings (holes) in portions corresponding to the reservoir 1 and the sample-dropping orifice 3 is adhered. The opening area of the opening formed in the operculiform part 8 for sealing and the cross section of each of the reservoir 1 and the sample-dropping orifice 3 are not necessarily equal to each other. A capillary 9 is connected to the tip of the passage 2 and the tip of the capillary 9 is inserted in the orifice 6 of the ion source 5. In a manner similar to the case of FIG. 1, by a pressure difference, a mobile phase solution is introduced from the reservoir 1 through the passage 2 into the capillary 9, runs off from the tip of the capillary 9 and is sprayed by the gas stream. In a manner similar to the case of FIG. 1, a sample dropped from the sample-dropping orifice 3 is also sent to the tip of the capillary 9 and sprayed by the gas stream to be thereby ionized.

Figure 3:
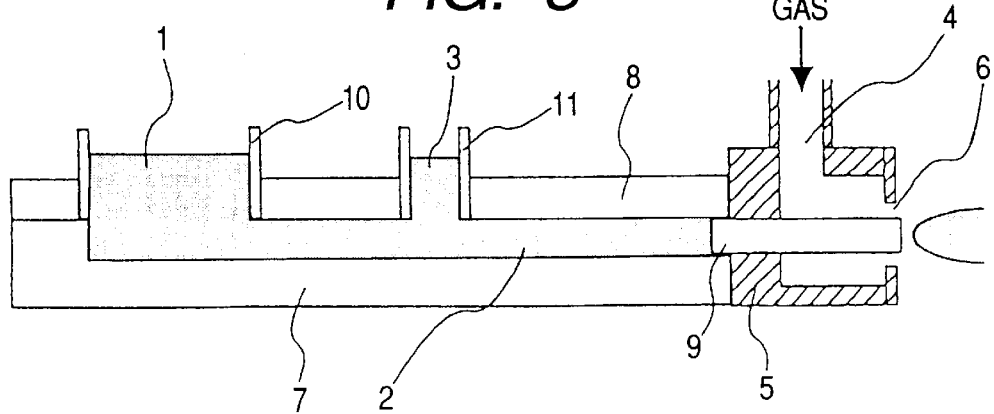
FIG. 3 is a cross section showing the construction of another modification of the sample-introduction tool as the first embodiment of the invention.

FIG. 3 shows the construction of a modification of the embodiment similar to that of FIG. 2, in which vessels 10 and 11 for storing the solution are attached to the reservoir 1 and the sample-dropping orifice 3, respectively. Since the vessel 10 is provided, a larger amount of a mobile phase solution can be stored in the reservoir 1, so that sample introduction/analysis of longer time can be realized. Since the vessel 11 is provided for the sample-dropping orifice 3, a change in liquid level can be addressed. As the material of those vessels, desirably, an inactive material which does not easily adsorb a chemical substance is used. In the case of using an active material, it is preferable to chemically treat the surface of the active material so as to become inactive.

Figure 4:
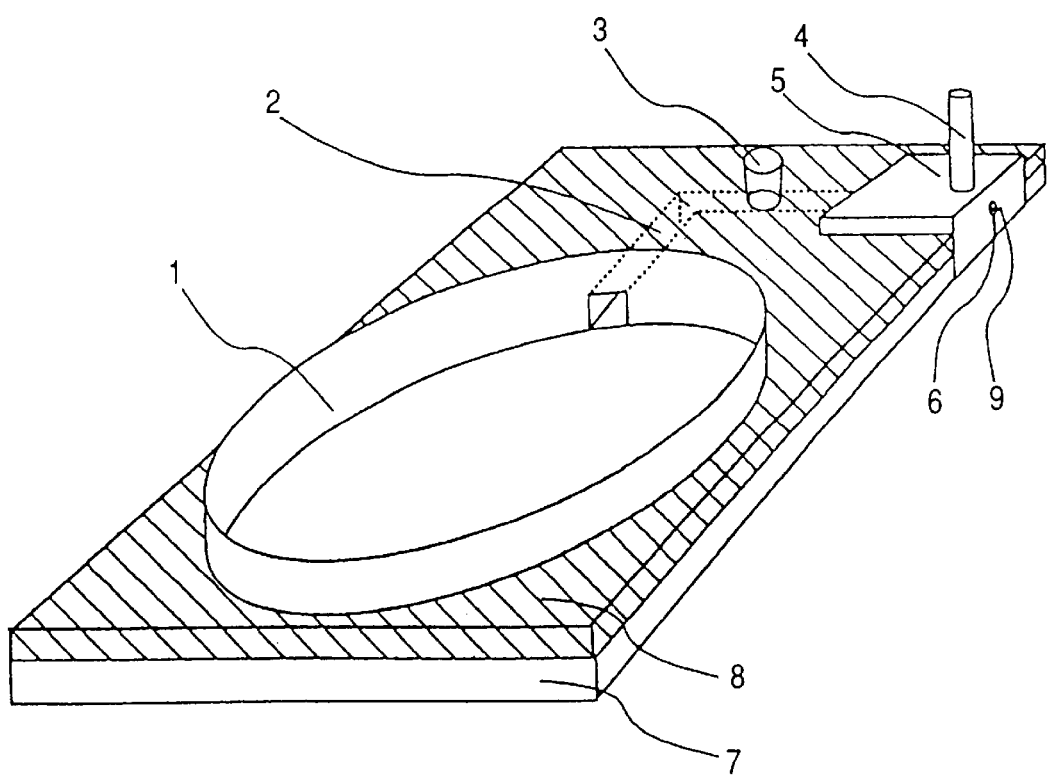
FIG. 4 is a bird's eye view of the sample-introduction tool shown in FIG. 3.

FIG. 4 is a bird's eye view of the structure of the tool shown in FIG. 3. As shown in FIG. 4, the passage 2 may be curved at its some midpoint, or the passage 2 and the capillary 9 of the ion source 5 may be arranged almost in a straight line. It is preferable to provide the sample-dropping orifice 3 to the ion source or nebulizer 5 side than the reservoir 1 side for the following reason. When the sample-dropping orifice 3 is provided on the reservoir 1 side, the injected sample is diluted by the mobile phase solution in the passage, and the analysis speed and analysis sensitivity deteriorate. An effect of sending the sample to the ion source or nebulizer 5 while suppressing the diffusion cannot be expected.

As described above, in the case of forming the reservoir 1, passage 2 and the like by etching a groove in the substrate 7, the grooves can be formed on the surface of the substrate 7 by using exposure and etching techniques for manufacture of a semiconductor device, so that a very small, a sample-introduction tool which can be integrated can be obtained.

<Second Embodiment>

Figure 5:
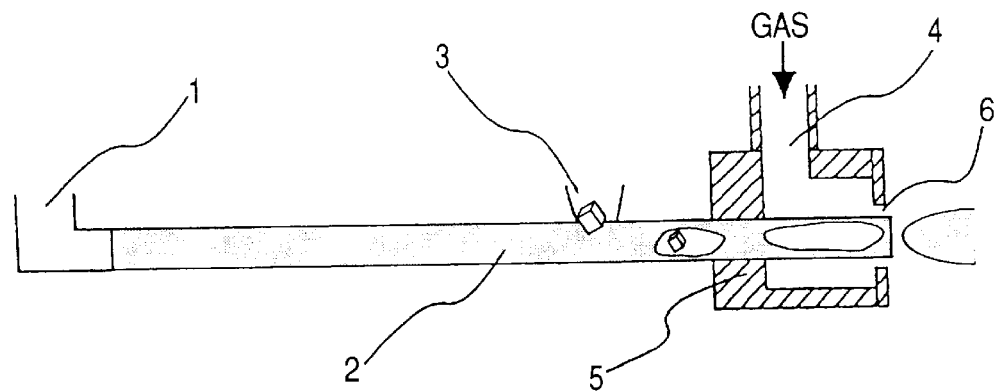
FIG. 5 is a cross section showing the basic construction of a sample-introduction tool as a second embodiment of the invention.

FIG. 5 shows the configuration of a tool as a second embodiment of the invention. In the second embodiment, the distance from the reservoir 1 to the sample-dropping orifice 3 in the passage 2 is made long and a part of the passage 2 also plays the role of the reservoir 1. In this case, the reservoir 1 can be formed small to a degree of playing the role of an inlet of the mobile phase solution. The mobile phase solution is stored in the long passage 2. The bottom portion of the reservoir 1 is connected to the passage 2 and the sample-dropping orifice 3 is opened at some midpoint in the passage 2. The length from the reservoir 1 to the sample-dropping orifice 3 is set to be longer than the length from the sample-dropping orifice 3 to the tip of the passage 2. The ion source 5 is disposed at the tip portion of the passage 2 and the tip portion of the passage 2 is inserted in the orifice 6 of the ion source 5. A solution spraying gas is passed from a gas supply source (not shown) on the outside via a gas passage 4 into the ion source 5, flows around the passage 2, and runs off from the orifice 6 to the outside atmosphere. When the speed of the outflow gas is high, the pressure around the tip of the passage 2 reduces, and a pressure difference occurs between the reduced pressure and the outside atmospheric pressure (normal atmospheric pressure) near the reservoir 1. By the pressure difference, the mobile phase solution stored in the reservoir 1 is pumped into the passage 2, sent to the tip of the passage 2 via the passage 2, and sprayed by the outgoing gas. The mobile phase solution injected from the reservoir 1 and filled in the passage 2 is sent by the pressure difference and the analysis can be continued until the border between the mobile phase solution and the external atmosphere comes just below the sample-dropping orifice 3. When the passage length from the reservoir 1 to the sample-dropping orifice 3 is sufficiently long, the analysis can be conducted for long time. In this case, even when time elapses and the volume of the mobile phase solution decreases, the level of the mobile phase solution in the part in contact with the outside atmosphere does not change, so that the solution can be sent at more stable speed. The sample dropped to the sample-dropping orifice 3 is also pumped into the passage 2 by the pressure difference between the pressure around the orifice 3 and the pressure around the tip of the passage 2, sent with the mobile phase solution to the tip of the passage 2, sprayed with a gas, and ionized. As described above, since the speed of sending the mobile phase solution is stable, the correspondence relation between the injected sample and the analysis result can be accurately grasped by time management. In the case of using an ion trap mass analyzer as the analyzer, analysis time of only the order of a millisecond is required. The sample to be analyzed can be therefore supplied in short time interval (less than hundreds milliseconds), and high-speed (high-efficiency) analysis can be carried out.

The cross section of the passage 2 may be almost constant, or the cross section on the ion source 5 side (tip side) may be smaller than that on the reservoir 1 side.

A sample may be a liquid sample or a solid state sample obtained by freezing a liquid sample. In the case of a liquid sample, since the liquid has surface tension, it is difficult to reduce the amount (a droplet) dropped per time to be smaller than the order of a microliter. However, in the case of the frozen sample, since there is no influence of the surface tension, the injection amount per time can be reduced to the order of a nanoliter. In the case of such a small frozen lamp, it is immediately melted into a mobile phase solution after being charged, so that there is no interfere with ionization.

Figure 6:
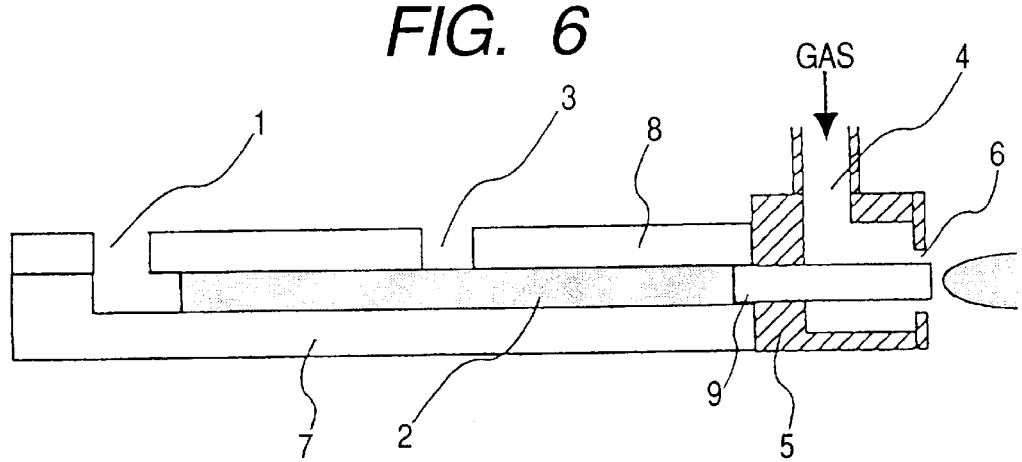
FIG. 6 is a cross section showing the construction of a modification of the sample-introduction tool as the second embodiment of the invention.

FIG. 6 shows the construction of a modification of the embodiment of FIG. 5, in which the reservoir 1, passage 2 and the like are formed by etching the substrate 7 and, by adhering the operculiform part 8 for sealing onto the substrate 7, the passage 2 is allowed to have the sealed structure. In the substrate 7, the reservoir 1 and the groove-shaped passage 2 are etched. On the substrate 7, the operculiform part 8 for sealing having openings (holes) in portions corresponding to the reservoir 1 and the sample-dropping orifice 3 is adhered. The opening (hole) area of the operculiform part 8 for sealing and the cross section of each of the reservoir 1 and the sample-dropping orifice 3 are not necessarily equal to each other. The capillary 9 is connected to the tip of the passage 2 on the substrate 7 and the tip of the capillary 9 is inserted in the orifice 6 of the ion source 5. In a manner similar to the case of FIG. 5, by a pressure difference, the solution is introduced from the reservoir 1 through the passage 2 into the capillary 9 and is sprayed by the gas stream. In a manner similar to the case of FIG. 1, a sample charged from the sample-dropping orifice 3 is also sent to the tip of the capillary 9 and sprayed by the gas stream, thereby ionized.

Figure 7:
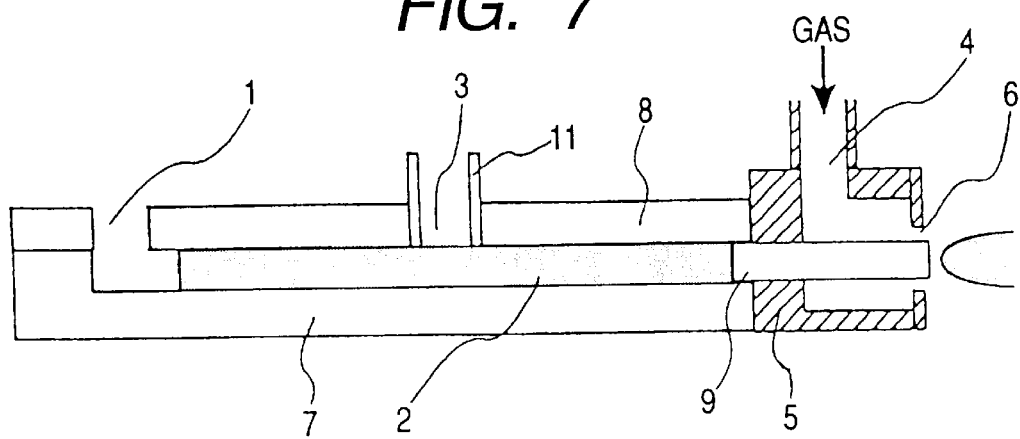
FIG. 7 is a cross section showing the construction of another modification of the sample-introduction tool as the second embodiment of the invention.

FIG. 7 shows the construction of a modification of the embodiment similar to that of FIG. 6, in which the vessel 11 for storing the solution is attached to the sample-dropping orifice 3. Since the mobile phase solution is stored in the long passage 2 and the reservoir 1 does not have to store a large volume of the mobile phase solution, there is no need to attach a vessel to the reservoir 1. As a matter of course, a vessel may be attached to the reservoir 1. By providing the sample-dropping orifice 3 with the vessel 11, a change in liquid level can be addressed. As the material of the vessel 11, an inactive material which does not easily adsorb a chemical substance may be used or the inner surface of the vessel may be chemically treated to be made inactive.

Figure 8:
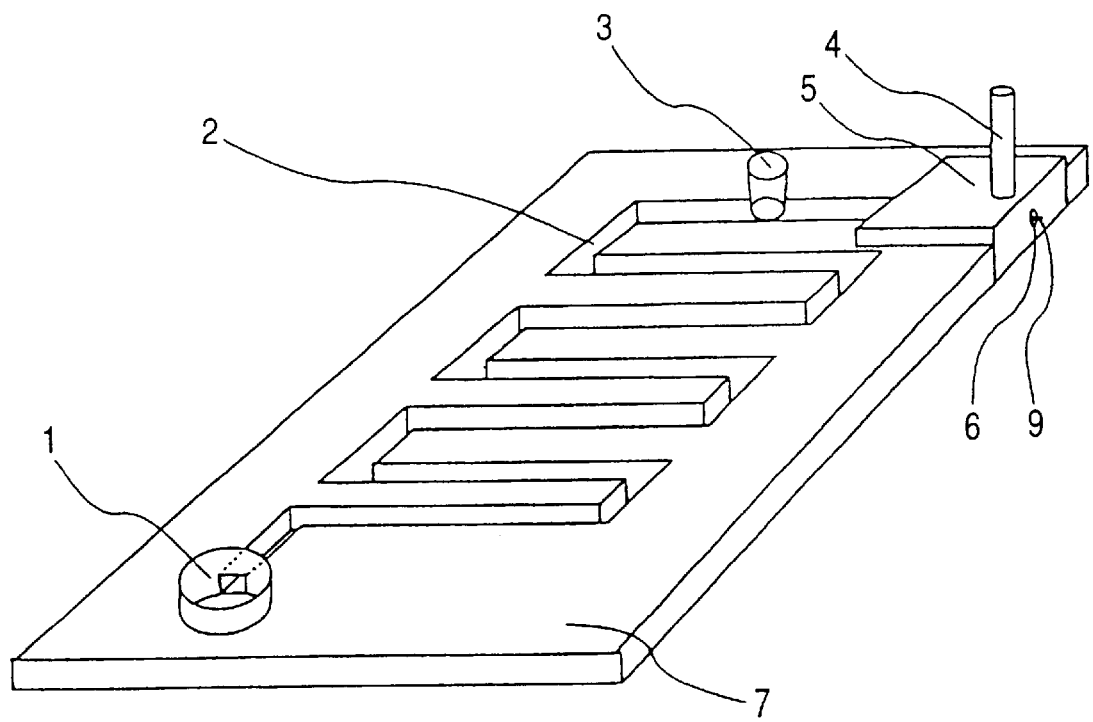
FIG. 8 is a bird's eye view of the sample-introduction tool shown in FIG. 7.

FIG. 8 is a bird's eye view of the structure of the tool shown in FIG. 7. In order to increase the length of the passage 2, the passage 2 may be curved. By forming the passage 2 in a spiral shape, the length of the passage 2 may be increased.

As described above, in the embodiment as well, the reservoir 1, passage 2 and the like are formed by etching the substrate 7. Consequently, by using exposure and etching techniques for manufacture of a semiconductor device, the tool can be easily manufactured.

<Conventional Technique as Reference>

Figure 9:
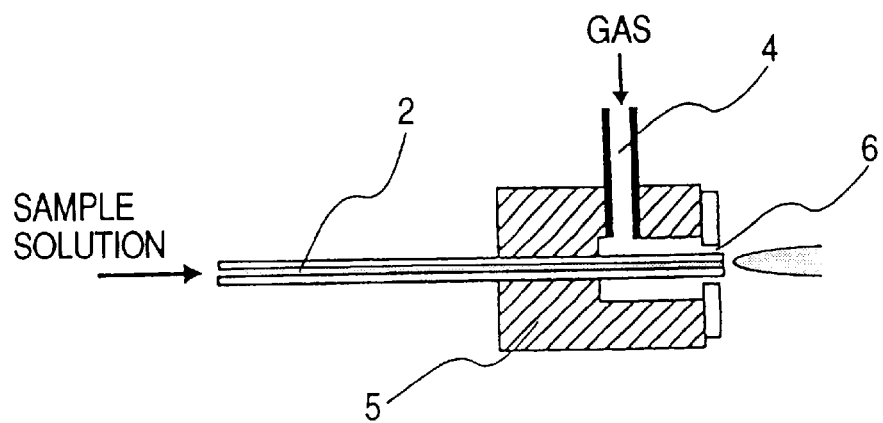
FIG. 9 is a cross section showing a schematic construction of a conventional sonic spray ion source.

FIG. 9 shows a conventional ion source of a system of performing ionization by spraying a solution with a gas stream. Ionization performed by spraying a solution with a high-speed gas stream is called "sonic spray ionization". An ion source in the method is used by being connected to a liquid chromatograph mass spectrometer. In this conventional ion source as well, a pressure difference occurs between both ends of the passage (capillary) 2 by a gas stream injected from the orifice 6, so that a small amount of the solution is pumped into the capillary 2. In practice, however, a large amount of the solution is introduced into the capillary 2 by a pump of the liquid chromatograph. Consequently, in a manner similar to ion sources in other ionization methods, a sample has to be introduced by using a valve.

Figure 10:
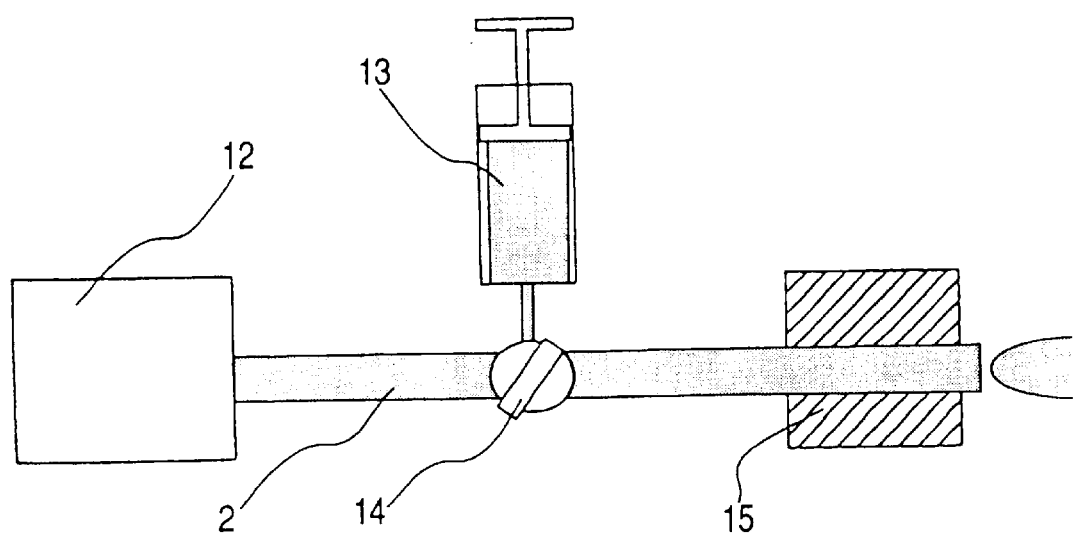
FIG. 10 is a schematic cross section showing the construction of a conventional sample-introduction tool.

FIG. 10 shows a conventional sample introducing method. A mobile phase solution is introduced by a pump 12 into the passage 2. A syringe 13 for introducing the sample is inserted to the passage 2. To prevent the mobile phase solution from flowing into the syringe 13, usually, the syringe 13 side is closed by a valve 14. At the time of introducing a sample, the flow of the mobile phase solution sent from the pump 12 is stopped by the valve 14, and the syringe 13 side is opened to inject the sample into the passage 2. After completion of the injection, the syringe 13 side is closed again and the valve 14 is switched so as to pass the mobile phase solution again. The injected sample is sent into an ion source 15 by the flow of the mobile phase solution and is ionized. When the sample is injected from the syringe 13 in a state where there is no valve 14, the sample solution flows backward to the pump 12 side and there is the possibility that the passage 2 is made unclean. Since the valve 14 is apt to be uncleaned, when analysis is performed many times, there is the possibility that contamination occurs. This problem similarly occurs in an ion source in sonic spray ionization or other ionization.

<Third Embodiment>

Figure 11:
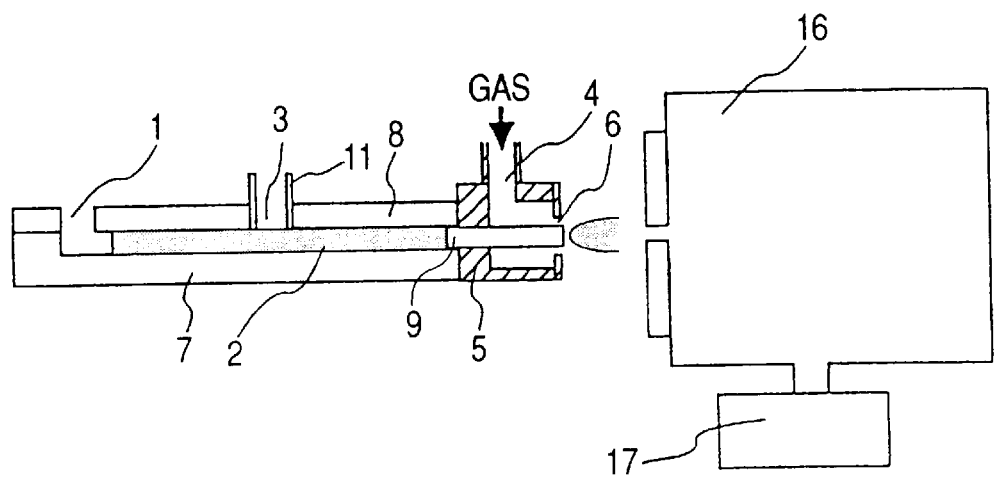
FIG. 11 is a schematic cross section showing the construction of a mass spectrometer as a third embodiment of the invention.

FIG. 11 is a diagram showing the construction of a case where an ion source is attached to a mass spectrometer according to the invention. A sample sprayed with a gas stream and ionized in atmosphere is introduced into a mass spectrometer 16 where mass spectrometry is performed. The inside of the mass spectrometer 16 is maintained under vacuum by a vacuum pump 17. As the mass spectrometer, any of a quadrupole mass spectrometer, three-dimensional quadrupole mass spectrometer, magnetic field type mass spectrometer, and the like can be used.

<Fourth Embodiment>

Figure 12:
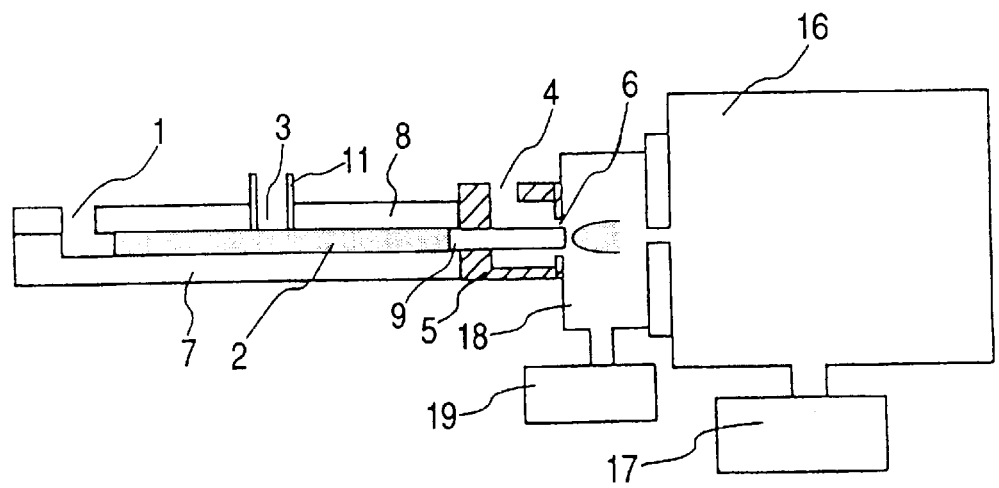
FIG. 12 is a schematic cross section showing the construction of a mass spectrometer as a fourth embodiment of the invention.

FIG. 12 shows further another embodiment of the invention. In the embodiment, the pressure around the end of the passage 2 is not reduced by a high-speed gas stream to cause a pressure difference between both ends of the passage 2, but a vacuum room 18 is provided between the ion source 5 and the mass spectrometer 16. The pressure in the vacuum room 18 is reduced by a vacuum pump 19 to cause a pressure difference between both ends of the passage 2, and the solution is sent in such a state. The vacuum room 18 is provided in contact with the orifice 6 side of the ion source 5. The ion source 5 and the vacuum room 18 are communicated with each other via the orifice 6. The capillary 9 is connected to the tip of the passage 2. The tip of the capillary 9 extends through the orifice 6 into the vacuum room 18. By the difference between the pressure in the vacuum room 18 and the pressure (usually, atmospheric pressure) on the reservoir 1 side, the solution in the passage 2 is pumped and sent. Meanwhile, when an air flows via the gas passage 4 into the ion source 5 and further flows via the orifice 6 into the vacuum room 18, the solution running out from the tip of the capillary 9 is sprayed and the sample contained in the solution is ionized. The vacuum room 18 is connected to the mass spectrometer 16 via a pore. A sample ion generated in the vacuum room 18 is introduced via the pore into the mass spectrometer 16 and is subjected to mass spectrometry.

Figure 13:
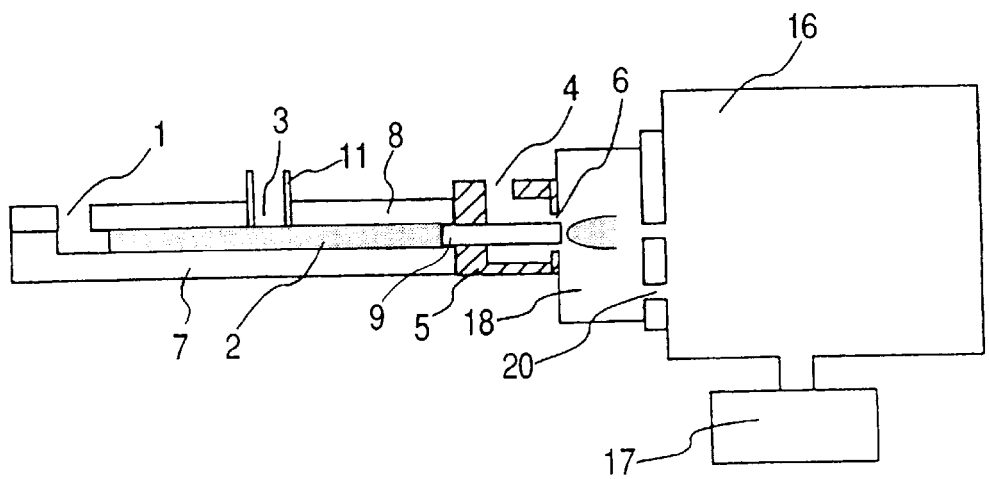
FIG. 13 is a schematic cross section showing the construction of a modification of the mass spectrometer as the fourth embodiment of the invention.

FIG. 13 shows the construction of a modification similar to that of FIG. 12, in which the vacuum room 18 and the mass spectrometer 16 are communicated with each other via an opening 20 for evacuation and the vacuum room 18 is also evacuated (pressure-reduced) by the vacuum pump 17 for evacuating the mass spectrometer 16.

Figure 14:
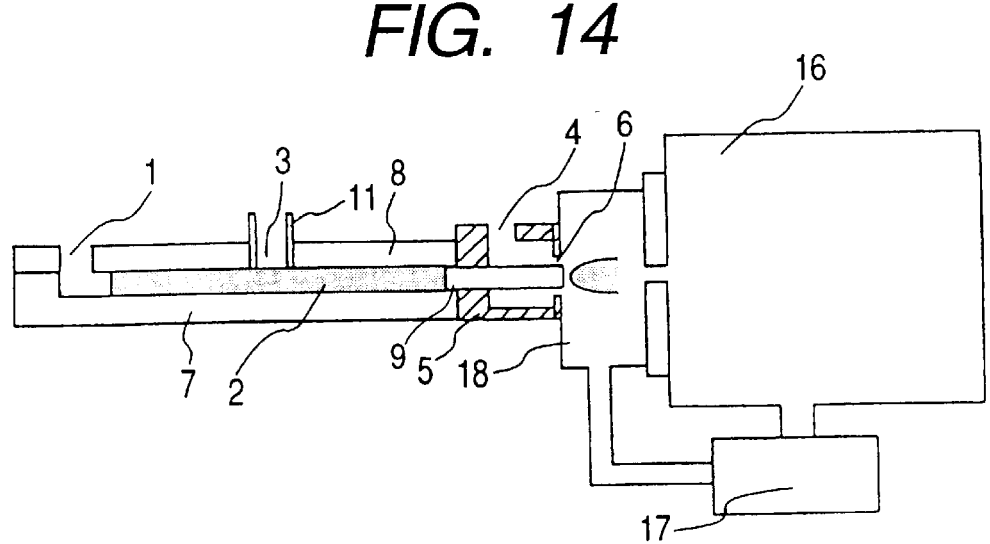
FIG. 14 is a schematic cross section showing the construction of another modification of the mass spectrometer as the fourth embodiment of the invention.

FIG. 14 shows the construction of a modification similar to those of FIGS. 12 and 13, in which the vacuum room 18 and the mass spectrometer 16 are evacuated (pressure-reduced) only by the single vacuum pump 17.

Figure 15:
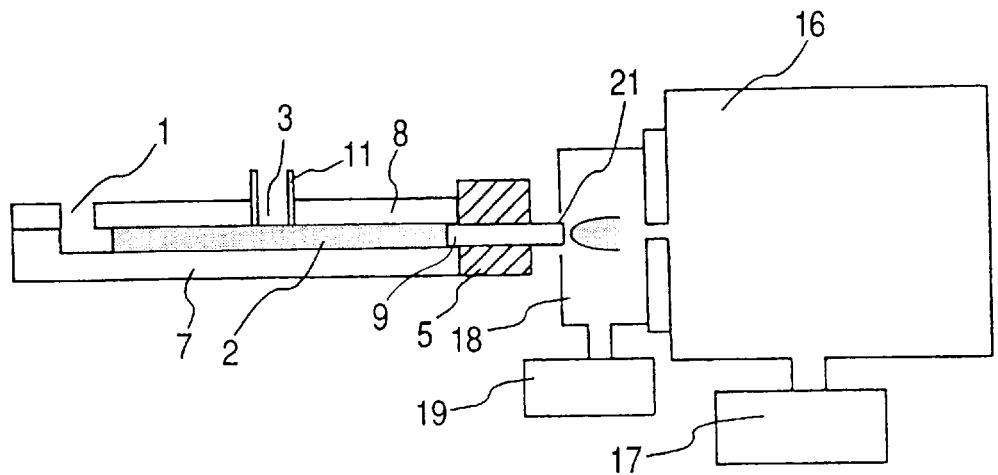
FIG. 15 is a schematic cross section showing the construction of further another modification of the mass spectrometer as the fourth embodiment of the invention.

FIG. 15 shows the construction of a modification similar to those of FIGS. 12 and 13, in which the ion source 5 is not provided with the gas introducing passage 4 and the ion source 5 and the vacuum room 18 are not in contact with each other. The ion source 5 and the vacuum room 18 are separated from each other, and the tip of the capillary 9 is inserted in an opening 21 for capillary insertion of the vacuum room 18. The pressure in the vacuum room 18 is reduced by a vacuum pump 19. Around the tip of the capillary 9, air flows via the opening 21 for capillary insertion into the vacuum room 18, the solution is sprayed by the air current, and the sample in the solution is ionized.

Figure 16:
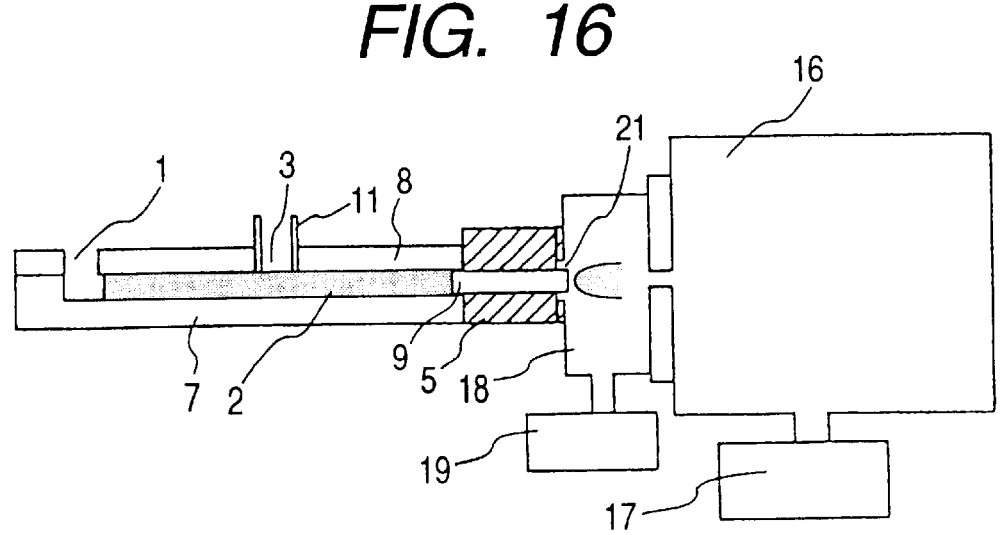
FIG. 16 is a schematic cross section showing the construction of further another modification of the mass spectrometer as the fourth embodiment of the invention.

FIG. 16 shows the construction of a modification of the embodiment of FIG. 15, in which the ion source 5 and the vacuum room 18 are in contact with each other. In the modification, there is no passage through which air flows into the vacuum room 18, so that the solution running off from the tip of the capillary 9 is not sprayed by the currents of air but is evaporated by a negative pressure in the vacuum room 18 and is ionized. An electrode (not shown) for discharging may be provided in the vacuum room 18 to ionize the sample by discharging.

<Fifth Embodiment>

Figure 17:
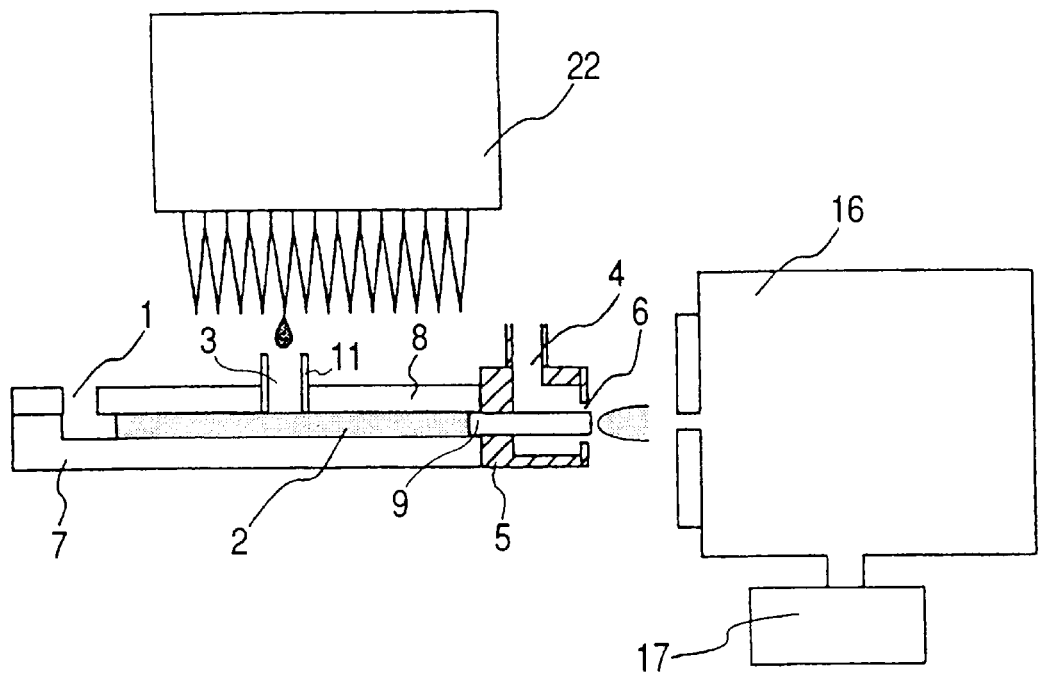
FIG. 17 is a schematic cross section showing the construction of a mass spectrometer system as a fifth embodiment of the invention.

FIG. 17 is a diagram showing the construction of a mass spectrometry system in which an autosampler for charging a sample solution is attached to the mass spectrometer according to the invention. A plurality of micropipets are attached to an autosampler 22, and the pipets are sequentially moved to charge samples into the passage 2 from the sample-dropping orifice 3. The samples may be continuously dropped or the sample and a buffer for cleaning may be alternately dropped. An autosampler of a type in which one pipet for sequentially taking samples from a plurality of sample vessels and dropping the samples may be also used.

<Sixth Embodiment>

Figure 18:
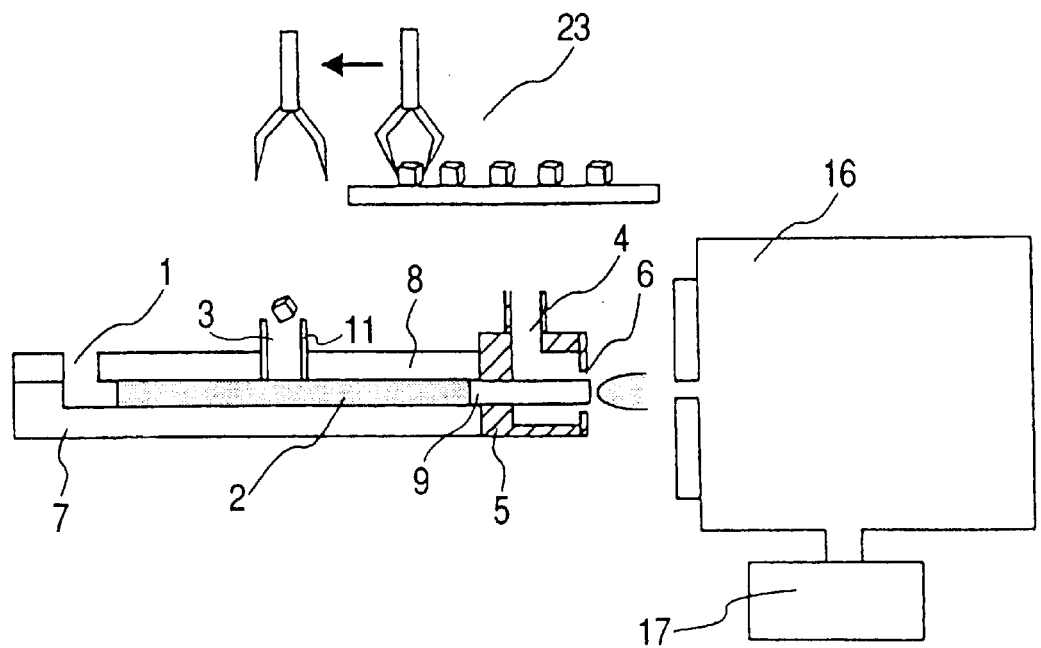
FIG. 18 is a schematic cross section showing the construction of a mass spectrometer system as a sixth embodiment of the invention.

FIG. 18 is a diagram showing the construction of a mass spectrometer system in which an autosampler for charging a solid sample into a mass spectrometer according to the invention is attached. An autosampler 23 sequentially drops a plurality of frozen samples from the sample-dropping orifice 3 into the passage 2. The sample dropping method may be a method of sequentially picking up and dropping samples by an arm, a method of reducing the pressure of a narrow tube, pumping a sample at the tip of the tube, carrying the sample over the sample-dropping orifice 3, and dropping. the sample by increasing the pressure in the tube, or a method of sequentially dropping samples by a belt conveyer. Further, the autosampler may have a cooling function so that the sample is not melted before it is dropped.

<Seventh Embodiment>

Figure 19:
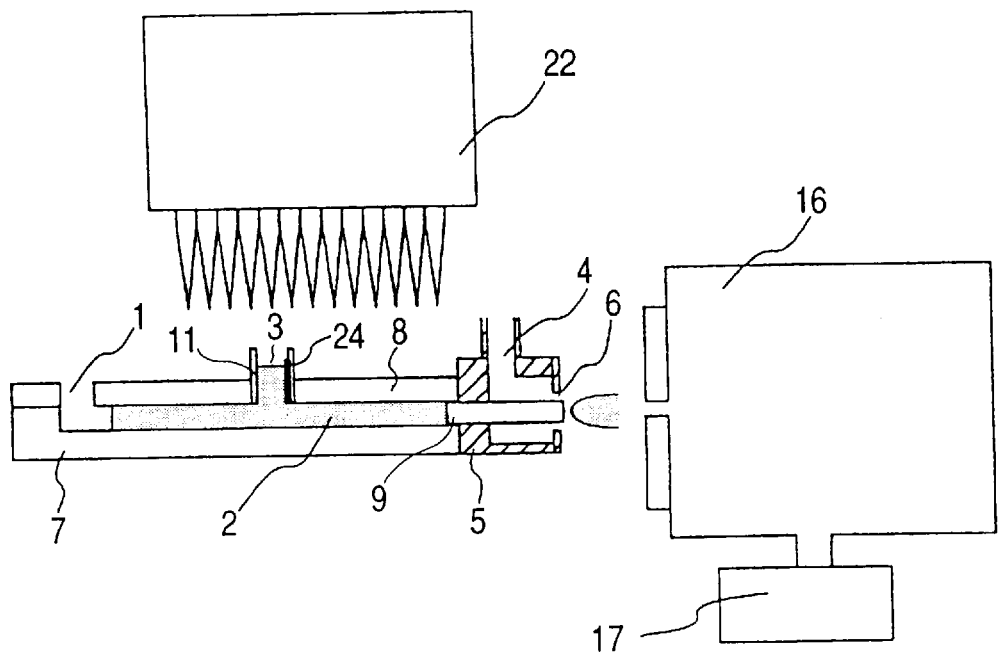
FIG. 19 is a schematic cross section showing the construction of a mass spectrometer system as a seventh embodiment of the invention.

FIG. 19 shows an embodiment in which a sensor for sensing the liquid level in the dropping orifice 3 is provided around the sample-dropping orifice 3 in FIG. 17. A liquid level sensor 24 senses the liquid level in the sample-dropping orifice 3 and feeds back the result to the autosampler 22 so that the liquid level does not go down excessively to prevent air from entering the passage 2 or that the next sample or buffer is charged before the liquid level goes down to a specific position. Obviously, the liquid level sensor may be similarly attached to the sample-dropping orifice 3 in FIG. 18.

It is also possible to construct in such a manner that the liquid level sensor 24 and the mass spectrometer operate interlockingly and analysis starts when the liquid level goes down to a specific position. Alternately, the analysis may be performed after elapse of specific time since the sample is dropped. The specific time may be a period of time since a sample is. dropped until a sample ion is trapped by the mass spectrometer. Obviously, the analysis can be continuously performed without limiting the analysis execution time.

Figure 20:
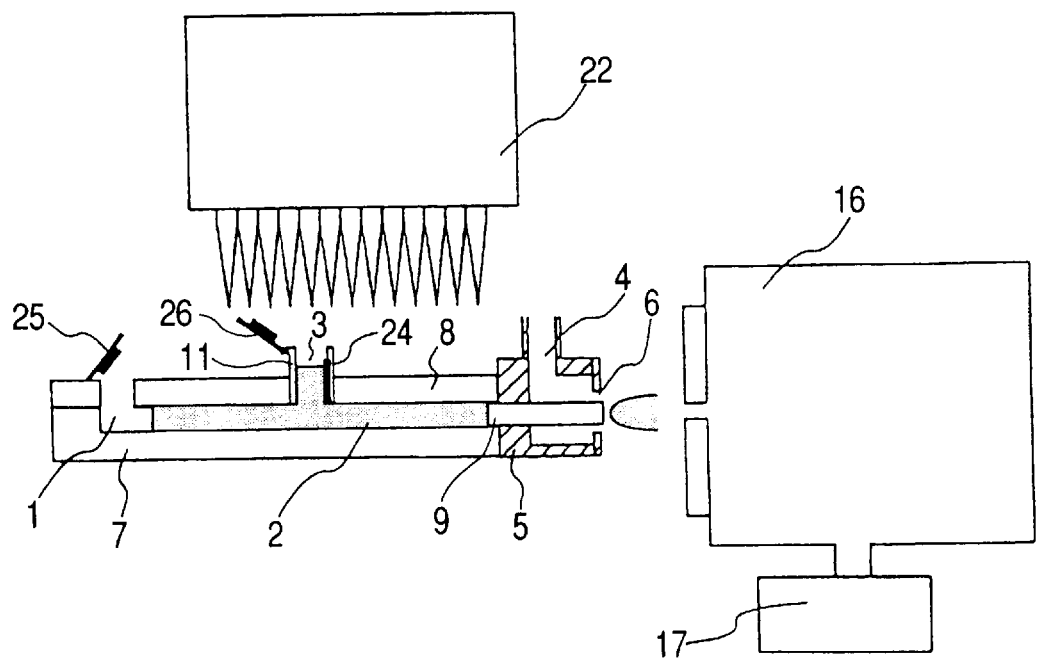
FIG. 20 is a schematic cross section showing the construction of a modification of the mass spectrometer system as the seventh embodiment of the invention.

FIG. 20 shows the construction of a modification of the embodiment of FIG. 19, in which a cover is provided for each of the reservoir 1 and the sample-dropping orifice 3. When a sample is dropped, a cover 26 is open and a cover 25 is closed, thereby adjusting so that the sample dropped into the sample-dropping orifice 3 preferentially flows in the passage 2. To prevent air from entering the passage 2 due to an excessive drop of the liquid level in the sample-dropping orifice 3, interlockingly with the liquid level sensor 24, when the liquid level goes down to a specific position, the cover 26 is closed and the cover 25 is opened to adjust so that a mobile phase solution from the reservoir 1 preferentially flows. The covers 25 and 26 may be mechanically opened/closed by using a motor, a spring, and the like or manually opened/closed. Needless to say, also in the case of dropping a solid sample to the sample-dropping orifice 3 as shown in FIG. 18, constructions similar to the above can be employed.

Figure 21:
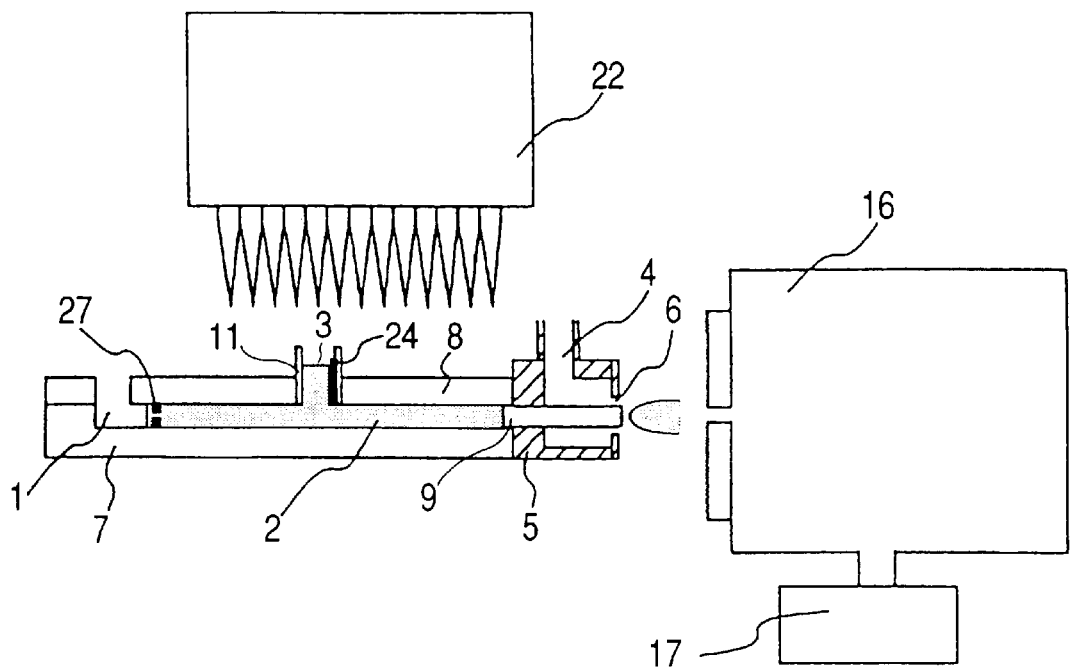
FIG. 21 is a schematic cross section showing the construction of another modification of the mass spectrometer system as the seventh embodiment of the invention.

FIG. 21 shows the construction of a modification in which an opening/closing valve 27 is provided between the end on the reservoir 1 side of the passage 2 and the sample-dropping orifice 3 in the embodiment of FIG. 19. Immediately after the sample is dropped, the opening/closing valve 27 is either closed or narrowed to reduce the flow rate of the mobile phase solution, thereby adjusting so that the dropped sample preferentially flows. On the other hand, when the liquid level sensor 24 senses that the liquid level in the sample-dropping orifice 3 goes down to a specific position, the opening/closing valve 27 is opened, thereby adjusting so that the mobile phase solution preferentially flows. It is also possible to provide a similar valve at the sample-dropping orifice 3 to adjust the amount of the samples dropped to the passage 2 or the liquid level in the sample-dropping orifice 3. Also in the case of dropping the solid-state samples into the sample-dropping orifice 3 as shown in FIG. 18, it is obvious that constructions similar to the above can be employed.

Figure 22:
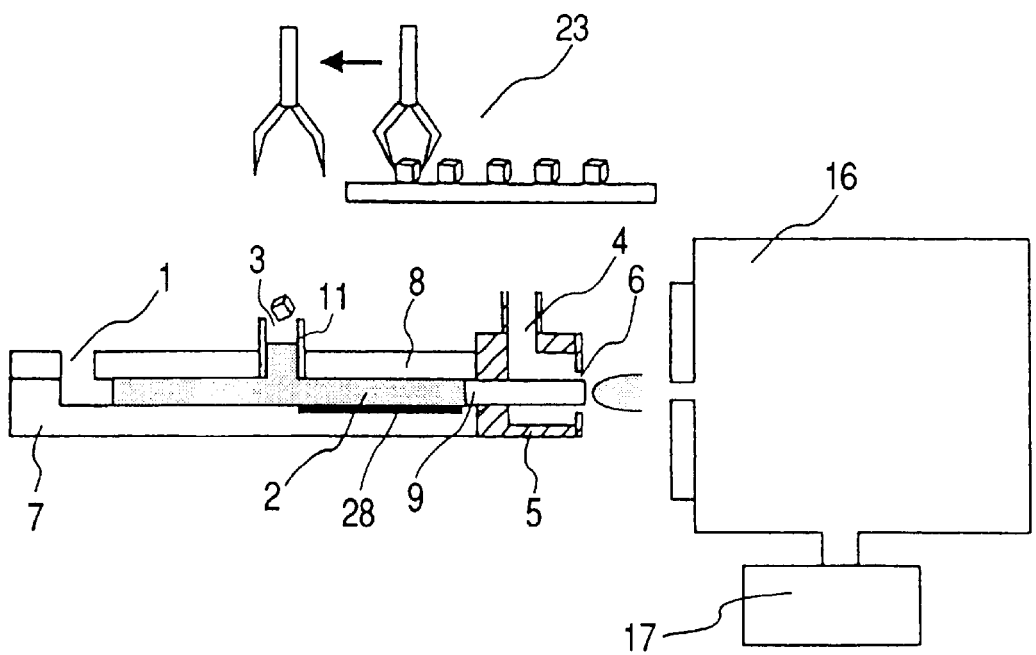
FIG. 22 is a schematic cross section showing the construction of further another modification of the mass spectrometer system as the seventh embodiment of the invention.

FIG. 22 shows the construction of a modification in which a sensor for sensing the position of a solid sample is disposed between the sample-dropping orifice 3 in the passage 2 and the tip of the passage 2. A sensor 28 senses the existing position of a sample dropped into the passage 2, when the sample arrives at a specific position, the autosampler 23 is interlockingly operated to drop the next sample. Alternately, the mass spectrometer is operated by a detection signal generated from the position sensor 28, thereby adjusting a timing of performing analysis. For example, analysis may be conducted either when the sample arrives at a specific position in the passage 2 or after elapse of predetermined time since the sample arrives at the specific position.

The construction example of FIG. 22 relates to the case of dropping the solid sample. Obviously, constructions similar to the above can be also employed in the case of dropping a sample solution. In the case of dropping a sample solution, a marker agent may be mixed in the sample dropped solution.

<Eighth Embodiment>

Figure 23:
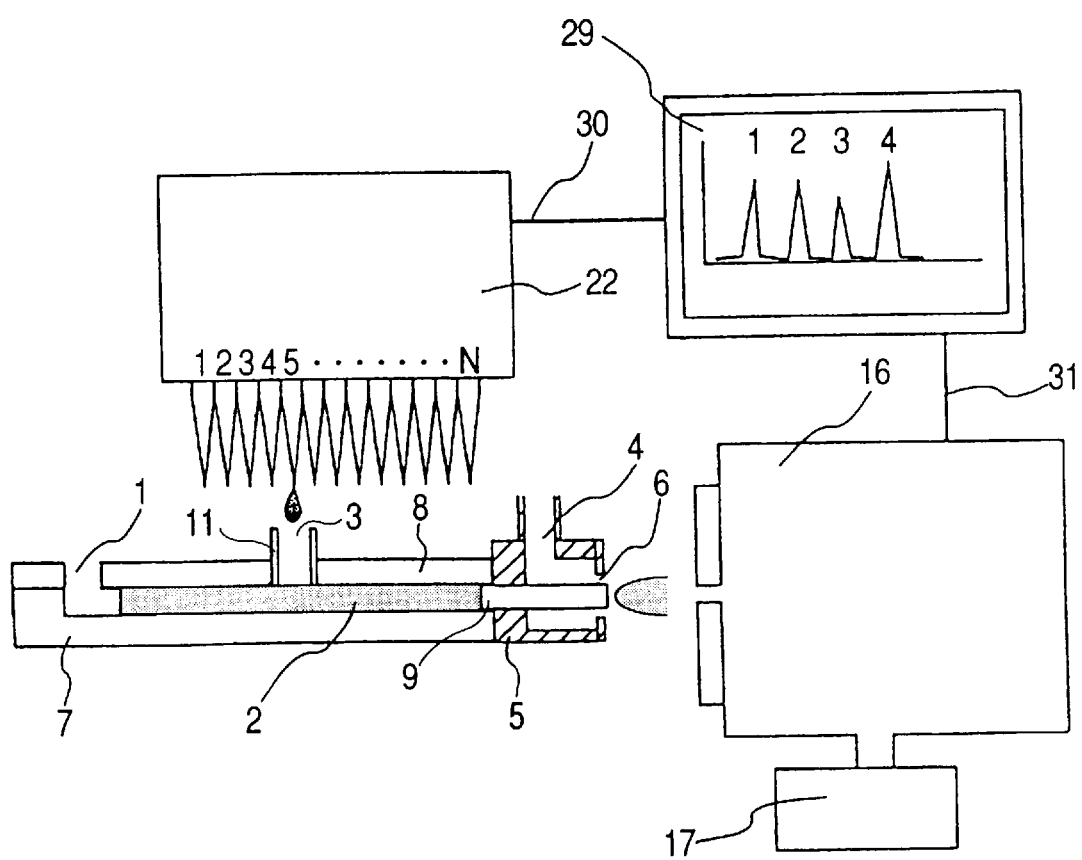
FIG. 23 is a schematic cross section showing the construction of a mass spectrometer system as an eighth embodiment of the invention.

FIG. 23 shows an embodiment in which a mass spectrometry system having an autosampler is further provided with a monitor 29 and numbers assigned to samples are displayed on the monitor 29 in association, with analysis results. Each of the pipets of the autosampler 22 is given a number for identifying a sample. In order to facilitate association of an analysis result of a sample dropped from each pipet with the kind of the dropped sample, the number for sample identification is also displayed near the analysis result displayed on the monitor 29. The monitor 29 is connected to the autosampler 22 and the mass spectrometer 16 via signal lines 30 and 31, respectively, so as to operate interlockingly and the number for sample identification is associated with the analysis result.

As an associating method, the result of the mass spectrometry performed after elapse of specific time since a sample is dropped may be used as the analysis result of the sample. By the time management based on a control signal for controlling the timing of dropping the sample solution, the corresponding relation between the dropped sample and the analysis result can be accurately grasped. It is also possible to dispose the liquid level sensor 24 or position sensor 28 as described above to sense the position of a dropped sample and associate the analysis result obtained when the dropped sample actually arrives at the mass spectrometer 16 or when it is expected that the dropped sample arrives at the mass spectrometer 16 with the dropped sample.

As described by the various embodiments, according to the invention, there is no need for providing the switching valve as conventionally provided for the sample-dropping orifice, so that contamination of a sample can be prevented. Since samples can be sequentially dropped with the sample-dropping orifice open, the throughput of analysis is improved.

The size of the sample-introduction tool itself can be reduced, contamination of the inside of the mass spectrometer can be minimized, and interrupted analysis time by a cleaning work can be reduced. Continuous analysis of long time can be therefore realized and the throughput of analysis is improved.

Industrial Applicability

The sample-introduction tool according to the invention can be used as effective means for introducing a small amount of a sample solution into an analyzer such as a mass spectrometer.

What is claimed is:

1. A sample-introduction tool comprising:

a reservoir for storing a solution opened to an outside atmosphere;

a passage of a sealed structure whose one end is connected to said reservoir and from whose other end said solution flowed in from said one end runs off;

an opening, provided at said passage, for introducing a sample into said passage; and a pressure reducing system for reducing pressure around said other end portion in said passage so as to be lower than pressure around said reservoir;

wherein said reservoir and said passage are formed on the same substrate.

2. A sample-introduction tool comprising:

a reservoir for storing a solution;

a passage of a sealed structure whose one end is connected to said reservoir and from whose other end, said solution flowed in from said one end runs off;

an opening, provided at said passage, for introducing a sample into said passage; and a pressure reducing system for reducing pressure around said other end of said passage so as to be lower than pressure around said reservoir, wherein said reservoir is opened to an atmosphere close to atmospheric pressure, said solution flowed from said reservoir into said passage is passed to said other end of said passage by a pressure difference between pressure in said atmosphere and pressure around said other end of said passage which is reduced to be lower than the pressure in said atmosphere, and the sample introduced from said opening into said passage is carried by a flow of the solution to said other end of said passage;

wherein said reservoir and said passage are formed on the same substrate.

3. A sample-introduction tool comprising:

a reservoir for storing a solution opened to outside atmosphere;

a passage of a sealed structure whose one end is connected to said reservoir and from whose other end, said solution flowed in from said one end runs off;

an opening, provided at said passage, for introducing a sample into said passage; and a gas nebulizer for nebulizing said solution run off from said other end of said passage by passing a gas to a portion around said other end of said passage;

wherein said reservoir and said passage are formed on the same substrate.

4. A sample-introduction tool comprising:

a reservoir for storing a solution;

a passage of a sealed structure whose one end is connected to said reservoir and from whose other end, said solution flowed in from said one end runs of;

an opening, provided at said passage, for introducing a sample into said passage; and a gas nebulizer for nebulizing said solution run off from said other end of said passage by passing a gas to a portion around said other end of said passage, wherein said reservoir is opened to atmosphere close to an atmospheric pressure, said solution flowed from said reservoir into said passage is passed to said other end of said passage by a pressure difference between pressure in said atmosphere and pressure around said other end of said passage which is reduced by a flow of said gas from said gas nebulizer so as to be lower than the pressure in said atmosphere, and the sample introduced from said opening into said passage is carried by a flow of the solution to said other end of said passage and is nebulized together with said solution by said gas nebulizer;

wherein said reservoir and said passage are formed on the same substrate.

5. The sample-introduction tool according to any one of claims 1 to 4, wherein said reservoir and said passage are formed on the same substrate made of at least one of silicon and quartz.

6. The sample-introduction tool according to claim 3 or 4, wherein said reservoir, said passage, and said gas nebulizer are formed on the same substrate.

7. The sample-introduction tool according to any one of claims 1 to 4, wherein said sample is in a liquid state or a solid state obtained by freezing a liquid state sample.

8. The sample-introduction tool according to any one of claims 1 to 4, wherein a vessel for storing said solution is additionally connected to an upper portion of said opening.

9. The sample-introduction tool according to claim 8, wherein an inner wall face of said vessel is made inactive by chemical treatment to prevent molecules of said sample from being adsorbed on said inner wall face.

10. The sample-introduction tool according to claim 8, wherein an inner wall face of said vessel is made of an inactive material to prevent molecules of said sample from being adsorbed on said inner wall face.

11. The sample-introduction tool according to any one of claims 1 to 4, wherein said reservoir is formed in a tubular structure.

12. The sample-introduction tool according to any one of claims 1–4, wherein a part of said passage is constructed so as to also play the role of said reservoir.

13. The sample-introduction tool according to claim 11, wherein length from said one end of said passage to said opening is longer than length from said opening to said other end of said passage.

14. The sample-introduction tool according to claim 11, wherein a cross section of said passage and that of said reservoir are almost equal to each other.

15. The sample-introduction tool according to any one of claims 1 to 4, wherein an opening is provided in said reservoir and said opening is provided with an opening/closing mechanism.

16. The sample-introduction tool according to any one of claims 1 to 4, wherein opening/closing means is provided for said opening.

17. The sample-introduction tool according to any one of claims 1 to 4, wherein flow control means for controlling the flow of said solution in said passage is provided between said reservoir and said opening.

18. The sample-introduction tool according to claim 17, wherein said flow control means is a valve.

19. The sample-introduction tool according to any one of claims 1 to 4, wherein a bottom face of said reservoir and that of said passage are almost at the same level.

20. The sample-introduction tool according to any one of claims 1 to 4, wherein a cross section of said passage on said other end side is set to be smaller than a cross section of said passage on said one end side.

21. The sample-introduction tool according to any one of claims 1 to 4 wherein electrodes are provided so as to be in contact with said solution in said reservoir and around said opening in said passage.

22. The sample-introduction tool according to claim 16, wherein liquid level detecting means for detecting liquid level of said solution is provided near said opening in said passage.

23. The sample-introduction tool according to claim 22, further comprising means for generating an instruction signal to close said opening with said opening/closing means when said liquid level of said solution goes down to specific level.

24. The sample-introduction tool according to claim 15, wherein liquid level detecting means for detecting liquid level of said solution is provided near said opening in said passage.

25. The sample-introduction tool according to claim 24, further comprising means for generating an instruction signal to close said opening with said opening/closing means when said liquid level of said solution is higher than specific level.

26. The sample-introduction tool according to claim 17, wherein liquid level detecting means for detecting liquid level of said solution is provided near said opening in said passage.

27. The sample-introduction tool according to claim 26, further comprising means for generating an instruction signal to control the flow of said solution in said passage by said flow control means when said liquid level of said solution is higher than specific level.

28. The sample-introduction tool according to any one of claims 1 to 4, further comprising solid matter detecting means for detecting a solid matter existing in said solution.

29. The sample-introduction tool according to claim 28, further comprising means for generating an instruction signal to additionally inject said sample to said opening when said solid matter in said solution detected by said solid matter detecting means arrives at a specific position.

30. An ion source comprising:
a reservoir for storing a solution opened to outside atmosphere;
a passage of a sealed structure whose one end is connected to said reservoir and from whose other end, said solution flowed in from said one end runs off;
an opening, provided at said passage, for introducing a sample into said passage; and
an ionizing unit for nebulizing said solution and said sample run off from said other end of said passage by passing a gas to a portion around said other end of said passage to thereby ionize said sample;
wherein said reservoir and said passage are formed on the same substrate.

31. An ion source comprising:
a reservoir for storing a solution;
a passage of a sealed structure whose one end is connected to said reservoir and from whose other end, said solution flowed in from said one end runs off;
an opening, provided at said passage, for introducing a sample into said passage; and
an ionizing unit for nebulizing said solution and said sample run off from said other end of said passage by passing a gas to a portion around said other end of said passage to thereby ionize said sample,
wherein said reservoir is opened to atmosphere close to an atmospheric pressure, said solution flowed from said reservoir into said passage is passed to said other end of said passage by a pressure difference between pressure in said atmosphere and pressure around said other end of said passage which is reduced by a flow of said gas from said gas nebulizer so as to be lower than the pressure in said atmosphere, and the sample introduced from said opening into said passage is carried by a flow of the solution to said other end of said passage, nebulized together with said solution by the flow of said gas from said ionizing means, and ionized;
wherein said reservoir and said passage are formed on the same substrate.

32. The ion source according to claim 30 or 31, wherein said reservoir and said passage are formed on the same substrate made of at least one of silicon and quartz.

33. The ion source according to claim 30 or 31, wherein said reservoir, said passage, and said ionizing unit are formed on the same substrate.

34. The ion source according to any one of claims 30 to 31, wherein said sample is in a liquid state or a solid state obtained by freezing a liquid state sample.

35. The ion source according to any one of claims 30 to 31, wherein a vessel for storing said solution is additionally connected to an upper portion of said opening.

36. The ion source according to claim 35, wherein an inner wall face of said vessel is made inactive by chemical treatment to prevent molecules of said sample from being adsorbed on said inner wall face.

37. The ion source according to claim 35, wherein an inner wall face of said vessel is made of an inactive material to prevent molecules of said sample from being adsorbed on said inner wall face.

38. The ion source according to any one of claims 30 to 31, wherein said reservoir is formed in a tubular structure.

39. The ion source according to any one of claims 30 to 31, wherein a part of said passage is constructed to also play the role of said reservoir.

40. The ion source according to claim 38, wherein length from said one end of said passage to said opening is longer than length from said opening to said other end of said passage.

41. The ion source according to claim 38, wherein a cross section of said passage and that of said reservoir are set to be almost equal to each other.

42. The ion source according to any one of claims 30 to 31, wherein an opening is provided in said reservoir and said opening is provided with an opening/closing mechanism.

43. The ion source according to any one of claims 30 to 31, wherein an opening/closing mechanism is provided for said opening.

44. The ion source according to any one of claims 30 to 31, wherein a flow control mechanism for controlling the flow of said solution in said passage is provided between said reservoir and said opening.

45. The ion source according to claim 44, wherein said flow control mechanism is a valve.

46. The ion source according to any one of claims 30 to 31, wherein a bottom face of said reservoir and that of said passage are almost at the same level.

47. The ion source according to any one of claims 30 to 31, wherein a cross section of said passage on said other end side is set to be smaller than a cross section of said passage on said one end side.

48. The ion source according to any one of claims 30 to 31, wherein electrodes are provided so as to be in contact with said solution in said reservoir and around said opening in said passage.

49. The ion source according to claim 43, wherein liquid level detecting means for detecting liquid level of said solution is provided near said opening in said passage.

50. The ion source according to claim 49, further comprising means for generating an instruction signal to close said opening by said opening/closing mechanism when said liquid level of said solution goes down to specific level.

51. The ion source according to claim 30 or 31, wherein liquid level detecting means for detecting liquid level of said solution is provided near said opening in said passage.

52. The ion source according to claim 51, further comprising means for generating an instruction signal to close said opening by said opening/closing mechanism when said liquid level of said solution is higher than specific level.

53. The ion source according to claim 44, wherein liquid level detecting means for detecting liquid level of said solution is provided near said opening in said passage.

54. The ion source according to claim 53, further comprising means for generating an instruction signal to control the flow of said solution in said passage by said flow control means when said liquid level of said solution is higher than specific level.

55. The ion source according to any one of claims 30 to 31, further comprising solid matter detecting means for detecting a solid matter existing in said solution.

56. The ion source according to claim 55, further comprising means for generating an instruction signal to additionally inject said sample to said opening when said solid matter in said solution detected by said solid matter detecting means arrives at a specific position.

57. A mass spectrometer comprising a sample-introduction tool according to any one of claims 1 to 4.

58. A mass spectrometer comprising an ion source according to any one of claims 30 to 31.

59. A mass spectrometer comprising:
   a sample-introduction tool according to any one of claims 1 to 4;
   an ionizing unit for ionizing a sample introduced from said sample-introduction tool;
   a vessel having a pore for introducing an ion from said ionizing unit; and
   an ion trap mass analyzer for performing mass analysis on the ion introduced into said vessel through said pore.

60. The mass spectrometer according to claim 59, further comprising a timing control unit for controlling a timing of introducing said sample into said passage in said sample-introduction tool.

* * * * *